(12) United States Patent
Müller et al.

(10) Patent No.: US 7,673,499 B2
(45) Date of Patent: Mar. 9, 2010

(54) RHEOMETER

(75) Inventors: Harald Müller, Stutensee (DE);
Michael Haist, Karlsruhe (DE); Jürgen Renkert, Karlsruhe (DE); Jörg Rich, Freiburg (DE)

(73) Assignees: Universitaet Karlsruhe, Karlsruhe (DE); Joerg Rich, Freiburg (DE)

( * ) Notice: Subject to any disclaimer, the term of this patent is extended or adjusted under 35 U.S.C. 154(b) by 279 days.

(21) Appl. No.: 11/797,922

(22) Filed: May 9, 2007

(65) Prior Publication Data
US 2007/0261478 A1    Nov. 15, 2007

(30) Foreign Application Priority Data
May 13, 2006   (DE)   ........................ 10 2006 022 316

(51) Int. Cl.
*G01N 11/14*   (2006.01)
(52) U.S. Cl. ..................................... 73/54.28
(58) Field of Classification Search ................. 73/54.28
See application file for complete search history.

(56) References Cited
U.S. PATENT DOCUMENTS

| | | | |
|---|---|---|---|
| 4,157,036 A * | 6/1979 | Kivenson .................. 73/290 R |
| 5,821,407 A * | 10/1998 | Sekiguchi et al. .......... 73/54.28 |
| 6,065,330 A * | 5/2000 | Freeman et al. ............ 73/54.28 |
| 6,481,267 B1 * | 11/2002 | Iles et al. .................... 73/54.28 |
| 6,708,554 B2 * | 3/2004 | Hettwer et al. ............. 73/54.43 |
| 6,997,045 B2 * | 2/2006 | Wallevik et al. ........... 73/54.28 |
| 7,021,123 B2 * | 4/2006 | Wallevik et al. ........... 73/54.02 |
| 7,201,040 B2 * | 4/2007 | Bateson et al. ............. 73/54.28 |
| 7,287,416 B1 * | 10/2007 | Bi .............................. 73/54.28 |
| 7,392,842 B2 * | 7/2008 | Morgan et al. ........... 166/250.1 |
| 7,412,877 B1 * | 8/2008 | Bi .............................. 73/54.28 |

FOREIGN PATENT DOCUMENTS

DE      567 388        10/1966
WO   WO 2004/068103    8/2004

* cited by examiner

*Primary Examiner*—Hezron Williams
*Assistant Examiner*—Rodney T Frank
(74) *Attorney, Agent, or Firm*—Paul Vincent

(57) ABSTRACT

A rheometer comprises a container for receiving a material sample to be investigated, and a rotary driven rotor which can be immersed at least partially into the material sample. At least sections of an inner wall of the container are provided with a profile in order to prevent formation of a sliding layer between the material to be investigated and the inner wall. The profile is thereby formed by at least one, in particular, several profiling elements which are exchangeably held on the container.

9 Claims, 2 Drawing Sheets

RHEOMETER

This application claims Paris Convention priority of DE 10 2006 022 316.0 filed May 13, 2006 the complete disclosure of which is hereby incorporated by reference.

BACKGROUND OF THE INVENTION

The invention concerns a rheometer comprising a container for receiving a material sample to be investigated, and a rotary driven rotor which can be at least partially immersed into the material sample, wherein at least sections of an inner wall of the container have a profile.

In order to determine the rheological values of a material sample, the shearing stress and the deformation of the material sample must be exactly measured under a predetermined load and exactly defined ambient conditions. This is effected e.g. in a rotary rheometer as disclosed in U.S. Pat. No. 6,997, 045 B2. A rotary rheometer of this type has a cup-like container into which the material sample is disposed. A rotary driven measuring shaft has a rotor at its lower end, which is immersed into the material sample. Rotation of the rotor within the material sample produces reaction forces and moments which are detected and from which the rheological characteristic material values of the material sample can be calculated, thereby taking into consideration the parameters of the surroundings.

In particular, in polydisperse suspensions, such as e.g. fresh building material suspensions, the metrological determination of the rheological properties is problematic, in particular, due to local demixing and associated sliding phenomena. These demixing phenomena can cause a very distinct localized change in the composition and thereby in the rheological properties of the material sample, and substantially falsify the measurement result. The extent of this problem depends on the composition of the examined material sample and also on the shearing stress which is produced in the contact zone between the material sample and the corresponding components of the rheometer.

In order to prevent formation of an undesired sliding zone, in particular, on the inner wall of the container, the inner wall of the container is conventionally provided with a profile. In particular, the inner wall surface of cylindrical sample containers, which are particularly suited for cement-containing suspensions, is provided with a groove structure having a depth of approximately 1 mm. This produces a toothing between the material sample and the inner wall of the container, which at least reduces the risk of sliding layer formation. In order to reliably prevent formation of a sliding layer, the profile of the inner wall of the container must be adjusted to the material being investigated. Since the groove structure is an integral component of the container, the profile cannot be adjusted to the material to be investigated.

It is the underlying purpose of the invention to provide a rheometer of the above-mentioned type with which the profile can be adjusted in a simple and fast manner to the type and properties of the material sample to be investigated.

SUMMARY OF THE INVENTION

This object is achieved in accordance with the invention with a rheometer having the features of the independent claim. The profile on the inner wall of the container is thereby formed by at least one and, in particular, several profile elements which are exchangeably fastened to the container. The user can thereby select the type and dimensions of the profile in dependence on the material to be investigated, and mount corresponding profiling elements on the container. It is thereby possible to reliably prevent formation of a sliding layer on the surface of the inner wall of the container through suitable selection of the profile geometry, wherein the profile also prevents excessive demixing phenomena in the material.

The profiling elements which are mounted to the container can be formed by head-like projections, wherein e.g. a plurality of pins or heads are mounted to the inner wall of the container at mutual separations from each other. In a preferred embodiment of the invention, the profiling elements are lamellas which form strip like ribs on the inner wall of the container, wherein the ribs should extend in the longitudinal direction of the container, i.e. substantially parallel to the axis of rotation of the rotor or its measuring shaft.

In one embodiment of the invention, the profiling elements extend over approximately the entire height of the container, thereby ensuring that the material sample is in contact with the profiling elements on the inner wall of the container over its entire filling height.

The profiling elements should preferably be substantially uniformly distributed about the periphery of the container. When the profiling elements form strip-shaped ribs, these can be distributed at a constant mutual separation or angular offset about the entire inner wall of the container. Alternatively, the profiling elements or ribs may also be distributed in an irregular arrangement about the inner periphery of the container.

In one embodiment of the invention, all profiling elements may project past the inner wall of the container into its inner space by the same length. As an alternative, profiling elements may be used which protrude by different lengths and which can be distributed in a recurrent sequence or completely arbitrarily about the inner periphery of the container.

The cross-sectional shape of the ribs may differ in dependence on the type of the material to be investigated. Profiling elements are preferably used which form ribs with a rectangular or polygonal cross-section. The ribs may, however, also have a cross-section that tapers towards the center of the container, e.g. a triangular cross-section.

The edge or surface of the rib that faces radially inwardly may preferably extend in a rectilinear fashion. Alternatively, it may also be corrugated or serrated in the longitudinal direction of the rib, extend in a radially inward convex or concave shape, or be otherwise curved.

The number of ribs disposed in the container also depends on the type of material to be investigated, wherein even one single rib may optionally be reasonable. In a rheometer having conventional dimensions, the number of ribs distributed about the periphery of the inner wall of the container is $\geq 4$ and in particular $\geq 20$. The mutual separation of the ribs should thereby preferably be $\geq 1$ mm and, in particular, $\geq 2$ mm, in order to provide sufficient toothing between the material to be investigated and the inner wall of the container.

When the rheometer is used to determine the rheological characteristic values of building materials, such as mortar or concrete, the holder of the exchangeable profiling elements must be relatively stable and have a simple construction, since the material to be investigated could otherwise impair the holder and, in particular, the exchangeability of the profiling elements. In a preferred embodiment of the invention, the container therefore has several holes in its wall, into each of which a profiling element can be inserted from the outer side of the container. The profiling elements are thereby preferably positively held in their inserted position in that e.g. defined abutment surfaces come into contact. This profiling element holder is advantageous in that it must only be forced radially outwardly and thereby be pushed out of the holes in the wall of the container in order to exchange it. In the inserted state, the profiling elements are tightly fitted in the holes to prevent formation of gaps into which the material to be investigated could enter.

Excessive motion of the profiling elements towards the center of the inner space of the container is positively prevented as mentioned above. During operation, a locking element should additionally be provided on the outer side of the container to keep the inserted profiling elements in their position. Each profiling element may have its own separate outer locking element. In a design with particularly simple construction in accordance with the invention, all profiling elements have one single common locking element, which may e.g. be an outer cup into which the container can be tightly fitted. In this case, the profiling elements are substantially flush with the outer side of the container when they are inserted into the holes of the wall of the container, such that the container with inserted profiling elements can be inserted into the outer cup.

Further details and features of the invention can be extracted from the following description of an embodiment with reference to the enclose drawing.

DESCRIPTION OF THE PREFERRED EMBODIMENT

Figure 1:
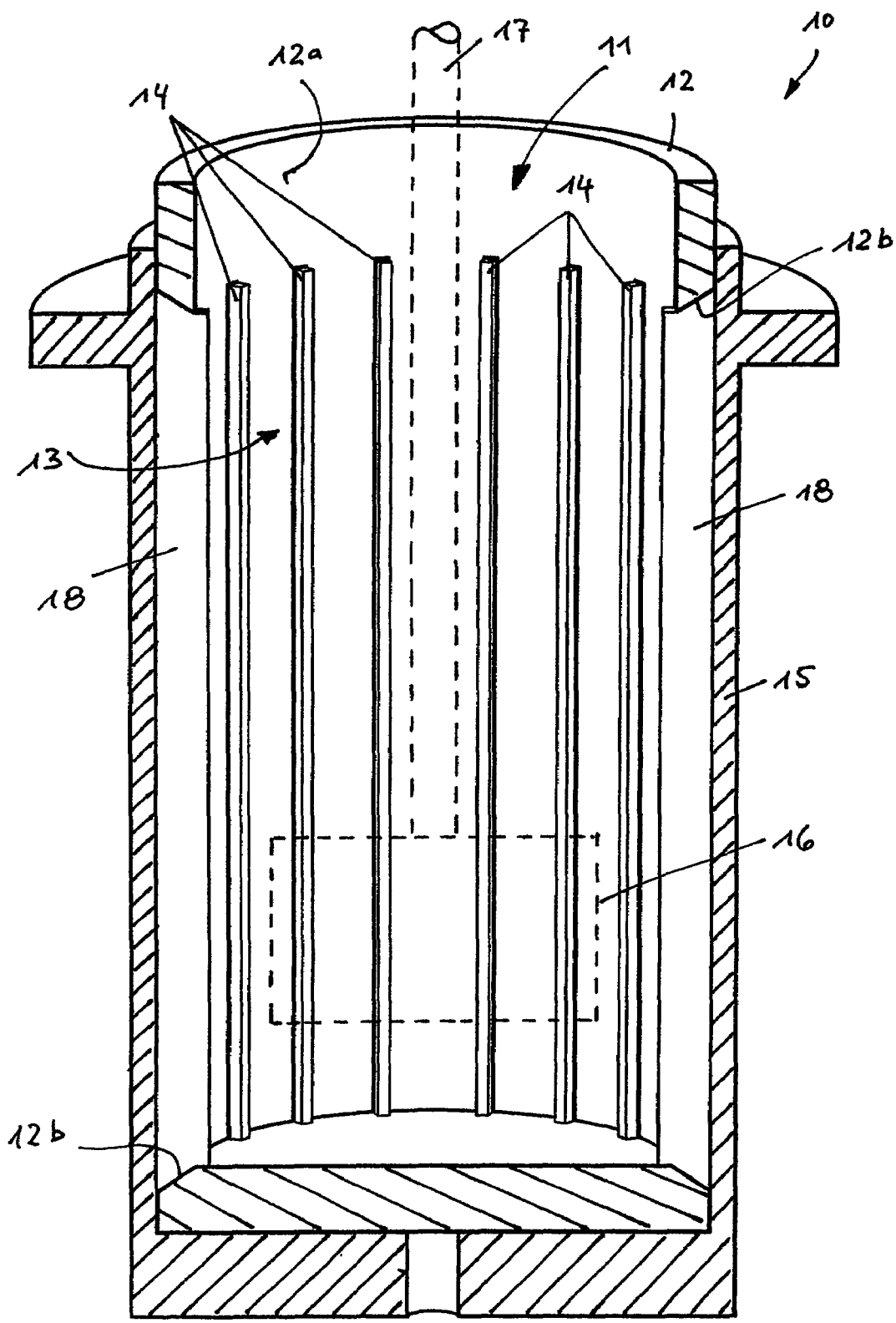
FIG. 1 shows a vertical section through a container of a rheometer.

FIG. 1 shows a section of the construction of a rheometer 10 comprising a cup-shaped container 12 which is open to the top and has a circular cross-section in the embodiment shown. A material sample to be investigated (not shown) can be filled into the inner space 11 of the container 12.

A vertical rotary driven measuring shaft 17 (shown as dashed lines) extends to the inner space 11 of the container 12 and has a rotor 16 at its lower end, which may have any shape or a shape which is adjusted to the material to be investigated.

A profile 13 is provided on the inner wall 12a of the container 12, which is formed by a plurality of strip-shaped ribs 14 which are distributed about the inner periphery of the container 12. Each rib 14 extends from the vicinity of the bottom of the container 12 to its upper area and extends substantially parallel to the measuring shaft 17 and thereby substantially vertically.

Each rib 14 is part of a lamella 18 that is exchangeably held on the container 12 and can be removed from the container 12, independently of the other lamellas 18. Towards this end, each lamella 18 has a hole 12b in the wall of the container 12. The lamella 18 can be inserted from the outer side of the container 12 into the hole 12b until it projects radially inwards from the inner wall 12a of the container 12 and forms the rib 14 (see FIG. 2).

Each hole 12b has inclined limiting walls at its upper and lower ends, such that the cross-section of the holes 12b tapers towards the center of the container 12. The lamellas 18 have a corresponding complementary shape such that they can be inserted into the holes 12b from the outer side of the container 12 until their upper and lower sides abut the associated walls of the holes (FIG. 1). In the inserted state, the outer side of the lamellas 18 is flush with the outer surface of the container 12.

When the container 12 has been provided with the lamellas 18 and thus has the profile 13 in the form of ribs 14 on its inner wall 12a, it is tightly fitted into an outer cup 15. The outer cup 15 secures the position of the lamellas 18 and prevents them from being forced to the outer side of the container 12 or even out of the container.

Figure 2:
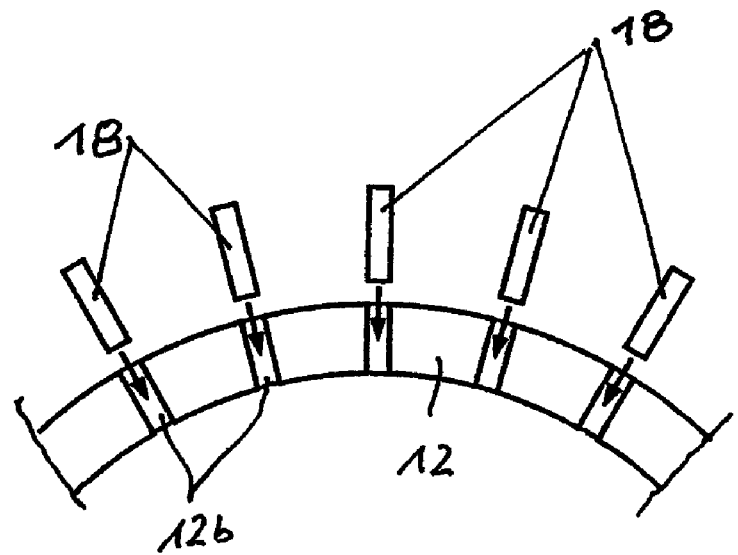
FIG. 2 shows portions of a horizontal section through the container prior to insertion of the profiling elements.
Figure 3:
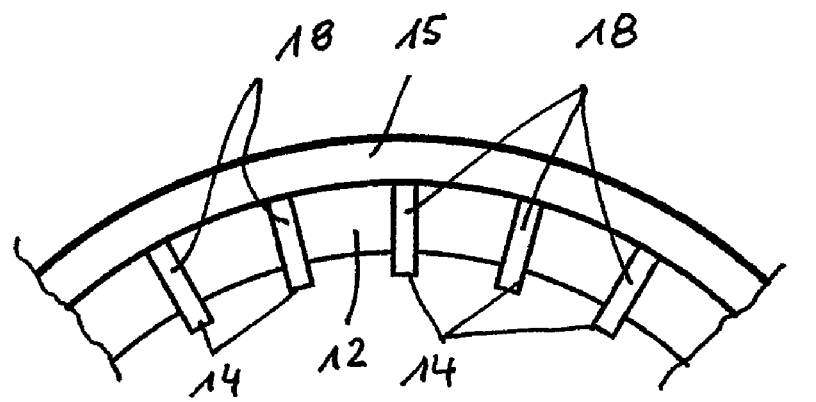
FIG. 3 shows a view in correspondence with FIG. 2 after insertion and securing of the profiling elements.
Figure 4:
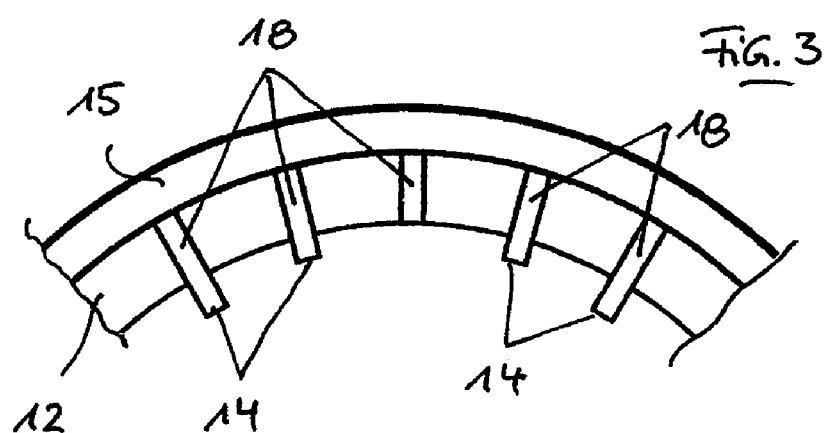
FIG. 4 shows a view in correspondence with FIG. 3 with the use of different profiling elements.

FIGS. 1 through 3 show a design, wherein a plurality of similar lamellas 18 are used to form similar ribs 14 which are substantially uniformly distributed over the inner periphery of the container 12. Alternatively, the container 12 may be provided with a profile 13 which is formed by ribs 14 which project by different lengths into the inner space of the container 12. In accordance with FIG. 4, at least one lamella 18 may fill the associated hole 12b, which does not project past the inner wall 12a of the container 12 but is flush therewith. One thereby obtains a profile which is uniformly distributed about the inner periphery of the container 12, which permits very good adjustment to the material to be investigated.

We claim:

1. A rheometer for analysing a material sample, the rheometer comprising;
   a container for receiving the material sample;
   a rotary driven rotor which is at least partially immersed into the material sample; and
   a profile disposed on at least sections of an inner wall of said container, said profile having profiling elements that are exchangeably held on said container, said container wall having several holes into each of which one of said profiling elements can be inserted from an outer side of said container.

2. The rheometer of claim 1, wherein said profiling elements are lamellas which form strip-like ribs on said inner wall of said container.

3. The rheometer of claim 2, wherein said ribs extend substantially in a longitudinal direction of said container.

4. The rheometer of claim 1, wherein said profiling elements extend through approximately an entire height of said container.

5. The rheometer of claim 1, wherein said profiling elements are substantially uniformly distributed about a periphery of said container.

6. The rheometer of claim 1, wherein said profiling elements project past an inner wall of said container by equal lengths.

7. The rheometer of claim 1, wherein said profiling elements project past said inner wall of said container by different lengths.

8. The rheometer of claim 1, further comprising at least one locking element disposed on said outer side of said container to keep an inserted said profiling element in position.

9. The rheometer of claim 8, wherein said locking element comprises an outer cup into which said container is tightly fitted.

* * * * *